(12) United States Patent
Ekimoto

(10) Patent No.: US 8,252,837 B2
(45) Date of Patent: Aug. 28, 2012

(54) TAMIBAROTENE CAPSULE PREPARATION

(75) Inventor: Hisao Ekimoto, Tokyo (JP)

(73) Assignee: TMRC Co., Ltd., Tokyo (JP)

( * ) Notice: Subject to any disclaimer, the term of this patent is extended or adjusted under 35 U.S.C. 154(b) by 11 days.

(21) Appl. No.: 12/593,866

(22) PCT Filed: Mar. 28, 2008

(86) PCT No.: PCT/JP2008/056073
§ 371 (c)(1),
(2), (4) Date: Sep. 29, 2009

(87) PCT Pub. No.: WO2008/120711
PCT Pub. Date: Oct. 9, 2008

(65) Prior Publication Data
US 2010/0048708 A1  Feb. 25, 2010

(30) Foreign Application Priority Data

Mar. 30, 2007 (JP) ................................ 2007-092604

(51) Int. Cl.
*A61K 31/195* (2006.01)
*A61K 9/48* (2006.01)

(52) U.S. Cl. ........................................ 514/563; 424/452

(58) Field of Classification Search .................... None
See application file for complete search history.

(56) References Cited

U.S. PATENT DOCUMENTS

| | | | |
|---|---|---|---|
| 4,316,917 A * | 2/1982 | Antoshkiw et al. | 426/540 |
| 5,525,618 A | 6/1996 | Shudo et al. | |
| 5,703,128 A | 12/1997 | Shudo et al. | |
| 5,716,995 A | 2/1998 | Shudo et al. | |
| 5,767,146 A | 6/1998 | Shudo et al. | |

FOREIGN PATENT DOCUMENTS

| | | |
|---|---|---|
| AU | 609428 B2 | 5/1991 |
| CN | 1660064 A | 8/2005 |
| EP | 0 619 116 A3 | 10/1994 |
| JP | 61-76440 A | 4/1986 |
| JP | 5-25037 A | 2/1993 |
| JP | 7-17854 A | 1/1995 |
| JP | 10-251144 A | 9/1998 |
| JP | 3001632 B2 | 1/2000 |
| WO | WO 93/00891 A1 | 1/1993 |
| WO | WO-02/18322 A1 | 3/2002 |
| WO | WO-03/094897 A1 | 11/2003 |

OTHER PUBLICATIONS

Fanjul et al., "Potential Role for Retinoic Acid Receptor-γ in the Inhibition of Breast Cancer Cells by Selective Retinoids and Interferons", Cancer Research, Apr. 1, 1996, vol. 56, pp. 1571-1577.
Graul et al., "The Year's New Drugs", Drug News Perspect, vol. 19 No. 1, pp. 33-54, Jan. 2006.
Richardson, "Capsule Filling, Filling Two-Piece Hard Gelatin Capsules with Liquids", Reprintd from Tablets & Capsules, pp. 33-38, Jan. 2007.
Extended European Search Report dated Jan. 20, 2012 for Application No. 08739191.8.

* cited by examiner

*Primary Examiner* — Sreeni Padmanabhan
*Assistant Examiner* — Jody Karol
(74) *Attorney, Agent, or Firm* — Birch, Stewart, Kolasch & Birch, LLP

(57) ABSTRACT

The present invention provides a practical preparation form of Tamibarotene and dosage form thereof, which exhibit high absorptivity by the body with minimized toxicity, and which are safe and stable without any risk of contamination. It is provided a Tamibarotene capsule preparation which encapsulates a composition comprising an oil component as its base and Tamibarotene as an active ingredient dissolved in the base. It is preferred that the oil component be propylene glycol fatty acid esters or polyethylene glycols. It is also preferred that the Tamibarotene capsule preparation comprise 0.1-50 mg/mL of the Tamibarotene based on the oil component.

9 Claims, 1 Drawing Sheet

TAMIBAROTENE CAPSULE PREPARATION

TECHNICAL FIELD

The present invention relates to a Tamibarotene capsule preparation, particularly a Tamibarotene capsule preparation which is safe without any risk of contamination, exhibits excellent stability, and is easy to be taken.

BACKGROUND ART

Retinoic acid (Vitamin A acid) is a substance which has an extremely important physiological effect on life-support functions, such as differentiating developing immature cells into mature cells that have a characteristic function and facilitating cell growth. Clinically, it has been found that retinoic acid is useful in treatment of Vitamin A deficiency, keratosis of epithelial tissue, leukemia, and certain types of cancers. It has been found that various Vitamin A derivatives which have been synthesized hitherto also have similar biological activity, and those compounds which have retinoic acid-like biological activity, including retinoic acid, are called retinoids.

However, in cases where a retinoid is used as a therapeutic drug, the retinoid is accumulated in the body due to its high lipid solubility and as a result, there have been a risk of developing retinoic acid syndrome. Further, the intrinsic toxicity of retinoic acid, such as skin irritation and teratogenicity, is also problematic.

Tamibarotene, a type of retinoid, has already been marketed as tablets; however, presently, no coating process is applied in order to maintain a favorable oral absorptivity.

Tamibarotene has at least two crystal polymorphs, and type 1 crystal (Patent Document 1) which melts at 193° C. and type 2 crystal (Patent Documents 2 and 3) which melts at 233° C. are known.

However, the type 1 crystal has problems in that it is extremely difficult to prepare a uniform crystal since transitions between crystal forms readily occur with a physical impact, so that it is unsuitable as the raw material for mass preparation of a pharmaceutical product which has a uniform standard. On the other hand, it is known that the type 2 crystal has a high stability not only for a physical impact, but also for heat, temperature, light and the like.

Further, in conventional tablet techniques including the manufacturing technique according to Patent Document 3, since the oral absorptivity is emphasized, a sufficient attention has not presently been paid to chemical hazard.

Patent Document 1: Japanese Patent No. 3001632
Patent Document 2: Japanese Unexamined Patent Application Publication No. S 61-76440
Patent Document 3: WO 2002/018322

DISCLOSURE OF THE INVENTION

Problems to be Solved by the Invention

Therefore, an object of the present invention is to provide a practical preparation form of Tamibarotene and dosage form thereof, which exhibit high absorptivity by the body with minimized above-described toxicity, and which are safe and stable without any risk of contamination.

Means for Solving the Problems

The present inventor has conducted intensive studies, with consideration on the viewpoint such as the possibility of Tamibarotene to disperse during the tablet manufacture and chemical hazard such as teratogenicity and skin irritation of Tamibarotene for its high probability of coming into contact during use, to discover that a practical oral preparation in a preparation form in which there is a reduced risk of chemical hazard, which preparation exhibits a high absorptivity by the body with minimized toxicity and is also safe and stable without any risk of contamination, can be obtained, thereby completing the present invention.

That is, the Tamibarotene capsule preparation of the present invention encapsulates a composition comprising an oil component as its base and Tamibarotene as an active ingredient dissolved in the base.

In the Tamibarotene capsule preparation of the present invention, it is preferred that the above-mentioned oil component be propylene glycol fatty acid esters or polyethylene glycols, and that the preparation comprises 0.1-50 mg/mL of the above-mentioned Tamibarotene as an active ingredient based on the above-mentioned oil component. Also preferable is that the above-mentioned polyethylene glycols have an average molecular weight of 200-1500.

The Tamibarotene capsule preparation of the present invention is preferably for oral administration, and the capsule thereof may be a soft capsule or hard capsule. Further, it is preferred that the Tamibarotene capsule preparation of the present invention be used for blood cancer and solid cancer.

Effects of the Invention

According to the present invention, a practical preparation form of Tamibarotene and dosage form thereof, which exhibit high absorptivity by the body with minimized above-described toxicity and are safe and stable without any risk of contamination, can be provided.

BEST MODE FOR CARRYING OUT THE INVENTION

Figure 1:
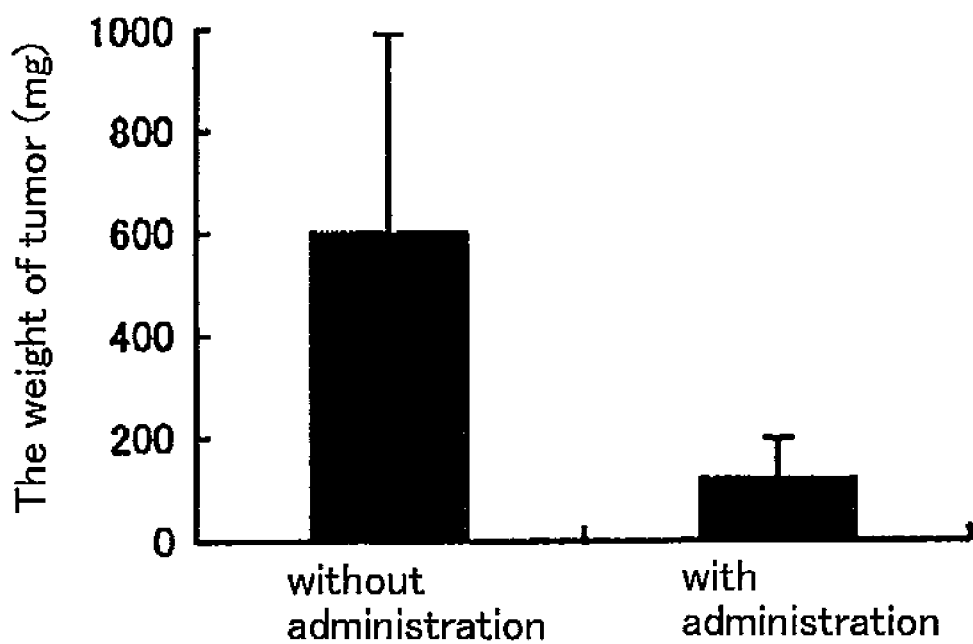
FIG. 1 is a graph showing in vivo growth inhibitory effect on $RAR\alpha(+)$ human breast cancer cells MCF-7.

The Tamibarotene capsule preparation of the present invention encapsulates a composition which comprises an oil component as its base and Tamibarotene as an active ingredient dissolved in the base.

The active ingredient of the present invention, Tamibarotene, is 4-[(5,6,7,8-tetrahydro-5,5,8,8-tetramethyl-2-naphthalenyl)carbamoyl]benzoic acid, may be a crystal or crystalline powder that is obtained by a conventional manufacture, and can be obtained, for example, by the methods described in Patent Documents 1-3.

Since Tamibarotene in a solution form is used for the Tamibarotene of the present invention, there is no need to consider crystal polymorphism and it is easy to produce the drug substance.

The oil component(s) used in the present invention can be any oil component with the proviso that it is in a liquid form when filled into a capsule and that it does not affect human body.

Specific examples of these oil components include one or more selected from the group consisting of esters of fatty acid and polyalcohol, polyethylene glycols, animal and plant oils, surfactants, and bases having low molecular weight.

In the Tamibarotene capsule preparation of the present invention, the esters of fatty acid and polyalcohol can be any ester with the proviso that it is in a liquid form when filled into a capsule and that it does not affect human body; however, it is preferred that the esters be a propylene glycol fatty acid esters, a sucrose fatty acid esters, a sorbitan fatty acid esters, and a fatty acid triglycerides.

In the Tamibarotene capsule preparation of the present invention, the propylene glycol fatty acid esters refer to all fatty acids; however, from the viewpoint of the solubility of Tamibarotene and marketability of the propylene glycol fatty acid esters, it is preferred that the esters be monooleate, di(capryl, caprylic acid)ester, and related fatty acid esters. Specific examples include RIKEMAL PO-100V (propylene glycol monooleate, manufactured by Riken Vitamin Co., Ltd.), Sun-Soft No. 25 ODV (Taiyo Kagaku Co., Ltd.), and the like.

Further, in the Tamibarotene capsule preparation of the present invention, $C_8$-$C_{12}$ medium chain triglycerides are preferred as the fatty acid triglycerides, and the examples thereof include 1-caprylyl-2,3-dilauryl glyceride, trinonanoyne glyceride, tricaprin glyceride, 1-lauro-2,3-dicaprin glyceride, 2-lauro-1,3-dicaprin glyceride, 1-capryl-2,3-dilauryl glyceride, 2-capryl-1,3-dilauryl glyceride, trilauryl glyceride, and the like.

Further, the oil component of the Tamibarotene capsule preparation of the present invention is preferably propylene glycol fatty acid esters or may be polyethylene glycols.

In the Tamibarotene capsule preparation of the present invention, the polyethylene glycols refer to polyethylene glycol, methoxypolyethylene glycol, and the like.

In the Tamibarotene capsule preparation of the present invention, it is also preferred that the polyethylene glycols be an essential component, and further that the polyethylene glycols have an average molecular weight of 200-1500.

Specifically, the polyethylene glycols refer to polyethylene glycols (Macrogols) 200, 300, 400, 600, 1000, 1500, or 1540, which are described in the Japanese Pharmacopoeia and the Japanese Pharmaceutical Codex, and one of them is usually used; however, in some cases, more than two of them may be used. For practical purposes, polyethylene glycols having an average molecular weight of 300, 400, 600, 1000, or 1540 are preferred.

Further, in cases where a polyethylene glycol (PEG) are used in the manufacture, it has to be in a liquid form in order to dissolve an additive when encapsulated into a soft capsule preparation. Therefore, it is handled at a temperature higher than the freezing point (° C.) of each polyethylene glycol, at which temperature the liquidity of each polyethylene glycol is maintained.

Specifically, with consideration of the absorptivity after oral administration, five kinds of PEG-200 (freezing point −50° C.), PEG-300 (freezing point −13° C.), PEG-400 (freezing point 7° C.), PEG-600 (freezing point 20° C.) and PEG-1000 (freezing point 37° C.) are preferred, and further, PEG-300, PEG-400, and PEG-600, which are in liquid form at room temperature and have an average molecular weight of 300, 400, and 600, respectively, are preferred.

Polyethylene glycols are nontoxic and have been used in various products and generally, they have been used as a base for many laxatives under the name such as Macrogol. Also, it is believed that polyethylene glycols withstand an extremely high osmotic pressure (several tens of atmospheric pressure) even when made into a membrane and that it does not exhibit specific interaction with biological materials.

In the Tamibarotene capsule preparation of the present invention, examples of the animal and plant oil include olive oil, sunflower seed oil, soybean oil, corn oil, fennel oil, sesame oil, safflower oil, wheat germ oil, perilla oil, camellia oil, whale oil, and the like.

As the other dissolving base, a surfactant such as polyoxyethylene hydrogenated castor oil and polysorbate, and base of low molecular weight may also be used.

Further, in the Tamibarotene capsule preparation of the present invention, especially when Tamibarotene is added to the oil solution, stirring procedure may be required if there is a possibility for the oil solution to be ununiform. However, since it is difficult to maintain the uniformity by stirring alone in many cases, the mixture is uniformly dispersed by adjusting the viscosity of the oil solution. Therefore, it is preferable to add an oil agent such as yellow bees wax, Japan wax, spermaceti wax, or hydrogenated vegetable wax, which agent is compatible with the oil solution and has a high melting point.

In the Tamibarotene capsule preparation of the present invention, it is preferred that, based on the calculation from the volume of the capsule, 0.1 mg/mL-50 mg/mL, preferably 0.5 mg/mL-30 mg/mL, more preferably 0.8 mg/mL-18.8 mg/mL of Tamibarotene be contained in the oil component. The effect of Tamibarotene may be insufficient when less than 0.1 mg/mL of Tamibarotene is contained in the oil component, while more than 50 mg/mL is not preferable from the viewpoint of solubility. Additionally, as the oil component, propylene glycol fatty acid esters, polyethylene glycols, surfactants, and bases having a low molecular weight are preferred.

The Tamibarotene capsule preparation of the present invention is produced by the following method. That is, in cases where a propylene glycol fatty acid esters or a polyethylene glycol whose average molecular weight is 200, 300, 400, or 600 is used, Tamibarotene drug substance is added thereto and the mixture is stirred until the Tamibarotene drug substance is dissolved uniformly therein at room temperature. Further, in cases where polyethylene glycol 1000, 1500, or 1540 is used, Tamibarotene drug substance is added thereto and the mixture is stirred until the Tamibarotene drug substance is dissolved uniformly therein while heating the polyethylene glycol to about 42° C. or higher in order to maintain it in a liquid condition. Subsequently, a given amount of the prepared mixed composition solution is filled into a soft capsule or hard capsule using a filling equipment. After the filling, the hard capsule is provided with a band sealing on the junction between the cap and the body of the capsule by using a solution mainly consisting of gelatin.

The capsule of the Tamibarotene capsule preparation of the present invention may be either a soft capsule or hard capsule, and is not particularly limited thereto with the proviso that the capsule is not deteriorated by its content, does not affect human body, and does not deteriorate its content. Further, a soft capsule preparation permits a liquid content to be contained therein.

Further, it is preferred that the size of the capsule be about 5 mm to about 12 mm in major axis for the soft capsule for clinical application, and the Japanese Pharmacopoeia capsules 1-4 are preferred for the hard capsule.

Further, the capsule of the Tamibarotene capsule preparation of the present invention is preferably for oral administration. It permits oral administration and unlike injection, reduces burden to patients.

Additionally, in a soft capsule preparation, administration over a prolonged period of time at a low concentration can also be attained by setting Tamibarotene content in a dose low.

Gelatin derived from a homeothermal animal such as cattle or swine has been used as the coating for conventional soft capsule preparations; however, a material derived from a plant can also be used for the capsule of the Tamibarotene capsule preparation of the present invention. Accordingly, issues posed by gelatin, such as vegetarianism and religious reasons, BSE problem, allergies, and high risk of infection and contamination compared to contaminants and pollutants of plant-derived material, can be reduced.

For the capsule of the capsule preparation of the present invention, as soft capsule which does not contain animal protein and is easy to dissolve, agar which has a jelly strength of not more than 300 g/cm$^2$ can be used. However, as agar is generally insoluble in water at 85° C. or less, to compensate this drawback, a plasticizer(s) such as edible high molecular substance (alginic acid and salts thereof, carrageenan, xanthan gum, gellun gum, Locust bean gum, dextrin, pullulan, and the like) and glycerin, sorbitol, and the like, is/are preferably included in the coating with agar, so that the capsule becomes compatible with the disintegration test according to the Japanese Pharmacopoeia and increases in its strength (Japanese Unexamined Patent Application Publication No. H7-196478). Accordingly, for patients using the capsule preparation of the present invention, there would be no boarder to personal use since the issues posed by vegetarianism and religious reasons can be resolved.

Further, in cases where gelatin is used, although there would be BSE problem from using gelatin made from bones as a raw material, the safety can be ensured by using epithelium as the raw material. Additionally, even when bones are used as the raw material, strict selection criteria for the raw material in the manufacture can eliminate BSE problem. Moreover, any gelatin can be used with the proviso that the content solution of the capsule does not adversely affect the coating; however, even in cases where there are some adverse effects, they can be resolved by using succinated gelatin.

It is preferred that the Tamibarotene capsule preparation of the present invention be used for blood cancer and solid cancer. Examples of blood cancer and solid cancer include, specifically, but are not limited to, blood cancers such as acute promyelocytic leukemia (APL) and multiple myeloma (MM), and solid cancers such as hepatoma, gastric cancer, breast cancer, esophageal cancer, prostate cancer, gynecologic cancer, pancreatic cancer, lung cancer, colon cancer, and the like.

The present invention can eliminate the risk of chemical hazard in the manufacture as well as in use, and be a preparation intended for oral or rectal administration. A high absorptivity by the body (bioavailability) can also be expected.

EXAMPLE

The present invention will be hereinafter explained in more detail by way of experiments and examples, but is not limited to these examples.
(Experiment)
Oil Component (Base) Solubility Test After precisely measuring 0.1 g of Tamibarotene and adding thereto 9.9 g of each base listed in Table 1, Tamibarotene was dissolved while warming in a water bath at about 60° C., and solubility test for Tamibarotene was conducted at room temperature, in a refrigerator at 35° C. (75% humidity), and at 60° C. The obtained results are shown in the Table 1 below.

TABLE 1

| | At room temperature | In a refrigerator | 35° C.-75% | (%) 65° C. |
|---|---|---|---|---|
| Macrogol 400R | 100 | 99.0 | 74.8 | 96.3 |
| Propylene glycol fatty acid ester | 100 | 101.0 | 100.3 | 100.5 |
| Triethyl citrate | 100 | 101.0 | 100.1 | 101.3 |
| Polysorbate 80 | 100 | 100.6 | 91.1 | 93.0 |
| Polyoxyethylene hydrogenated castor oil (35E.0.) | 100 | 101.8 | 93.7 | 94.5 |

As seen from the above Table 1, Tamibarotene exhibits an optimum solubility and stability in the dissolved solution in propylene glycol fatty acid ester.

Example 1

Tamibarotene drug substance in an amount of 10 g was added to 990 g of propylene glycol fatty acid ester, which was then stirred to obtain a uniformly dissolved solution. This solution was filled into oval soft capsules in an amount of 100 mg per capsule to obtain Tamibarotene capsule preparation containing 1 mg of Tamibarotene. Subsequently, they were made into finished products by PTP packaging.

The obtained Tamibarotene capsule preparation, after storage for 6 months under a hermetic condition and accelerating condition of the stability test (40° C., 75% relative humidity), did not exhibit any change in crystal precipitation and dissolved form as well as in disintegration test. Additionally, since the content was maintained at 95% or more in content measurement by high performance liquid chromatography method, the preparation had an excellent long-term storage stability at room temperature.

Example 1-1

Regarding to Oral Absorptivities of the Tamibarotene Capsule Preparation of the Present Invention and 2 mg of Amnolake (Registered Trademark) Tablet which is a Commercially Available Preparation (Experimental Method)
Four capsules of the soft capsule preparation of Example 1 (containing 1 mg of Tamibarotene) and, as comparative example, two of Amnolake tablet 2 mg which is a commercially available preparation, were administered orally to each beagle, and the pharmacokinetics parameters were estimated from the values of Tamibarotene blood level (a total amount of non-protein-bound Tamibarotene and bound-/unbound-Tamibarotene) which were obtained by cross-over trials to compare biological equivalence between the two preparations.
(Experimental Result)
Table 2 shows the area under the blood concentration time curve (AUC:nghr/mL), maximum drug concentration (Cmax:ng/mL), maximum drug concentration time (Tmax: h), and half-life period (T1/2:h). According to Example 1 in which the dogs were orally administered with soft capsule preparations, it is clear that the soft capsule preparations have bioavailability and absorption rate which are comparable to those of Amnolake tablet 2 mg which is commercially available, and thus the soft capsule preparation is useful as a preparation for oral administration which can resolve the drawbacks of Tamibarotene tablets.

Further, in an antitumor drug Tamibarotene which has a problem partly in the actual use, since the soft capsule preparation has good bioavailability and biological equivalence to Tamibarotene 2 mg tablet while reducing the side effect without any risk of contamination such as chemical hazard during manufacture and use, it is appreciated that use of anti-cancer agent in the clinical field can be attained, which agent is safe, reduces burden to a patient, and has an excellent storage stability.

TABLE 2

| Administration route | AUC (ng · h/mL) | Tmax (h) | T½ (h) | Cmax (ng/mL) |
|---|---|---|---|---|
| oral (2 mg tablet, 2 tablets) | 1819 | 1.0 | 4.3 | 286.47 |
| oral (1 mg soft capsule, 4 capsules) | 1616 | 2.0 | 4.6 | 211.77 |
| oral (2 mg tablet, 2 tablets) | 2697 | 2.0 | 4.2 | 352.64 |
| oral (1 mg soft capsule, 4 capsules) | 3329 | 2.0 | 4.3 | 469.92 |

Example 1-2

In Vivo Growth inhibitory Effect on RARα(+) Human Breast Cancer Cells MCF-7

(Experimental Method)
A graft of human breast cancer cells MCF-7 was hypodermically implanted to nude mice, and after orally administering 3 mg/kg/day of Tamibarotene for 28 days beginning 10 days after the implantation, the weight of tumor (mg) was measured.
(Experimental Result)
As shown in FIG. 1, Tamibarotene inhibited the growth of human breast cancer cells MCF-7.

Example 1-3

In Vivo Growth Inhibitory Effect of Retinoid on IL-6 Dependent RARα(+) Human Multiple Myeloma Cells U266

Figure 2:
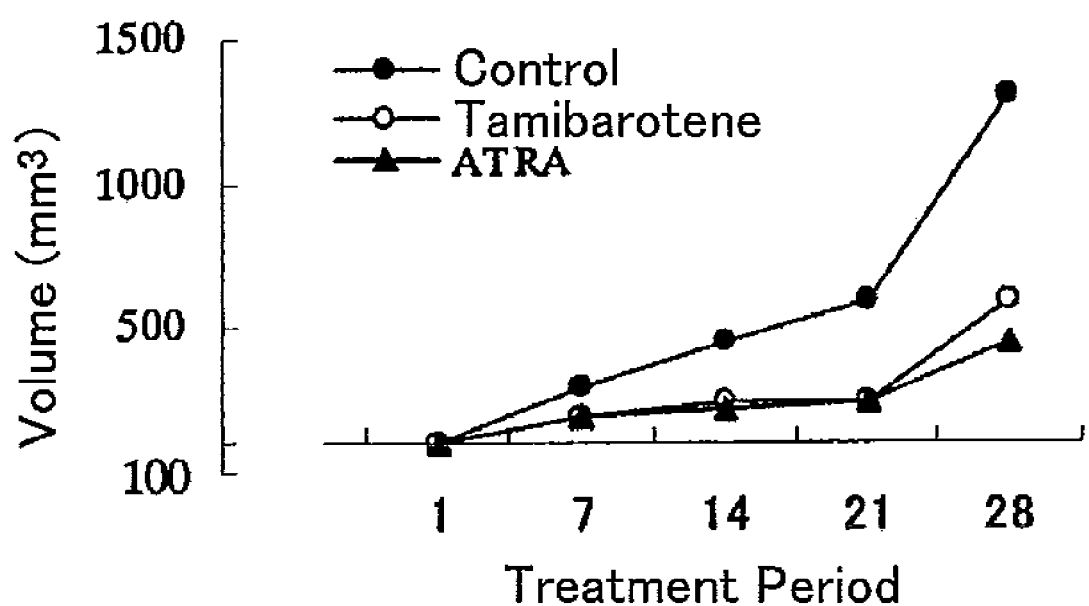
FIG. 2 is a graph showing in vivo growth inhibitory effect of the retinoid on IL-6 dependent $RAR\alpha(+)$ human multiple myeloma cells U266.

(Experimental Method)
IL-6 dependent RARα(+) human multiple myeloma cells U266 were hypodermically implanted to the flank of SCID mice, and after orally administering 3 mg/kg/day of Tamibarotene or 10 mg/kg/day of ATRA (all-trans retinoic acid) for 28 consecutive days beginning on the following day of the implantation, the volume of tumor was measured.
(Experimental Result)
As shown in FIG. 2, Tamibarotene and ATRA inhibited the growth of U266 cells.

Example 2

Tamibarotene drug substance in an amount of 10 g was added to 990 g of propylene glycol fatty acid ester, which was then stirred to obtain uniformly dissolved solution. This solution was filled into oval soft capsules in an amount of 100 mg per capsule to obtain Tamibarotene capsule preparation containing 1 mg of Tamibarotene. Subsequently, they were made into finished products by PTP packaging.

The obtained Tamibarotene capsule preparation, after storage for 6 months under a hermetic condition and accelerating condition of the stability test (40° C., 75% relative humidity), did not exhibit any change in crystal precipitation and dissolved form as well as in disintegration test. Additionally, since the content was maintained at 95% or more in content measurement by high performance liquid chromatography method, thus the preparation had an excellent long-term storage stability at room temperature.

Example 3

Tamibarotene drug substance in an amount of 20 g was added to 980 g of propylene glycol fatty acid ester, which was then stirred to obtain uniformly dissolved solution. This solution was filled into oval soft capsules in an amount of 100 mg per capsule (specific gravity 0.94) to obtain Tamibarotene capsule preparation containing 2 mg of Tamibarotene (18.8 mg/mL). Subsequently, they were made into finished products by PTP packaging.

The obtained Tamibarotene capsule preparation, after storage for 6 months under a hermetic condition and accelerating condition of the stability test (40° C., 75% relative humidity), did not exhibit any change in crystal precipitation and dissolved form as well as in disintegration test. Additionally, since the content was maintained at 95% or more in content measurement by high performance liquid chromatography method, thus the preparation have excellent long-term storage stability at room temperature.

Example 4

Tamibarotene drug substance in an amount of 0.1 g was added to 21 g of polyethylene glycol (hereinafter, abbreviated as PEG) 400, which was then stirred and uniformly dissolved to obtain a solution having a specific gravity of 1.13. This solution was filled into oval soft capsules at 0.19 mL per capsule (in an amount of 210 mg, assuming the specific gravity of 1.13) to obtain Tamibarotene capsule preparation containing 1 mg of Tamibarotene. Subsequently, they were made into finished products by PTP packaging.

Example 5

Tamibarotene drug substance in an amount of 0.1 g was added to 21 g of PEG 300, which was then stirred and uniformly dissolved to obtain a solution having a specific gravity of 1.13. This solution was filled into oval soft capsules at 0.19 mL per capsule (in an amount of 210 mg, assuming the specific gravity of 1.13) to obtain Tamibarotene capsule preparation containing 1 mg of Tamibarotene and they were subsequently made into finished products by PTP packaging.

Example 6

Tamibarotene drug substance in an amount of 0.1 g was added to 42 g of PEG 400, which was then stirred and uniformly dissolved to obtain a solution having a specific gravity of 1.13. This solution was filled into oval soft capsules at 0.19 mL per capsule (in an amount of 210 mg, assuming the specific gravity of 1.13) to obtain Tamibarotene capsule preparation containing 0.5 mg of Tamibarotene and they were subsequently made into finished products by PTP packaging.

Example 7

The solution of Example 4 was filled into oval soft capsules at 0.25 mL per capsule (in an amount of 280 mg, assuming the specific gravity of 1.13) to obtain Tamibarotene capsule preparation containing 0.7 mg of Tamibarotene and they were subsequently made into finished products by PTP packaging.

Example 8

Tamibarotene drug substance in an amount of 0.1 g was added to 21 g of PEG 600, which was then stirred and uniformly dissolved to obtain a solution having a specific gravity of 1.13. This solution was filled into oval soft capsules at 0.19 mL per capsule (in an amount of 210 mg, assuming the specific gravity of 1.13) to obtain Tamibarotene capsule preparation containing 1 mg of Tamibarotene and they were subsequently made into finished products by PTP packaging.

Example 9

Tamibarotene drug substance in an amount of 0.1 g was added to 141 g of PEG 400, which was then stirred and uniformly dissolved to obtain a solution having a specific gravity of 1.135. This solution was filled into oval soft capsules at 0.25 mL per capsule (in an amount of 280 mg, assuming the specific gravity of 1.13) to obtain Tamibarotene capsule preparation containing 0.2 mg of Tamibarotene and they were subsequently made into finished products by PTP packaging.

Example 10

As 21 g of Macrogol 1500 was being melted while heating at 45° C., 0.1 g of Tamibarotene drug substance was added thereto and dissolved to obtain a solution having a specific gravity of 1.13. This solution was filled into oval soft capsules at 0.19 mL per capsule (in an amount of 210 mg, assuming the specific gravity of 1.13) to obtain Tamibarotene capsule preparation containing 1 mg of Tamibarotene and they were subsequently made into finished products by PTP packaging.

Example 11

Tamibarotene drug substance in an amount of 0.1 g was added to 35 g of PEG 400, which was then stirred and uniformly dissolved to obtain a solution having a specific gravity of 1.13. This solution was filled into oval soft capsules at 0.31 mL per capsule (in an amount of 350 mg, assuming the specific gravity of 1.13) to obtain Tamibarotene capsule preparation containing 1 mg of Tamibarotene and they were subsequently made into finished products by PTP packaging.

Example 12

Tamibarotene drug substance in an amount of 0.1 g was added to 28 g of PEG 400, which was then stirred and uniformly dissolved to obtain a solution having a specific gravity of 1.13. This solution was filled into oval soft capsules at 0.25 mL per capsule (in an amount of 280 mg, assuming the specific gravity of 1.13) to obtain Tamibarotene capsule preparation containing 1 mg of Tamibarotene and they were subsequently made into finished products by PTP packaging.

Example 13

The solution of Example 10 was filled into oval soft capsules at 0.19 mL per capsule (in an amount of 210 mg, assuming the specific gravity of 1.13) to obtain Tamibarotene capsule preparation containing 0.8 mg of Tamibarotene and they were subsequently made into finished products by PTP packaging.

Example 14

Tamibarotene drug substance in an amount of 10 g was added to 990 g of propylene glycol fatty acid ester, which was then stirred to obtain a uniformly dissolved solution. This solution was filled into hard capsules of Japanese Pharmacopoeia capsule in an amount of 100 mg per capsule to obtain Tamibarotene capsule preparation containing 1 mg of Tamibarotene. They were subsequently sealed and then made into finished products by PTP packaging.

Example 15

Tamibarotene drug substance in an amount of 10 g was added to 990 g of propylene glycol fatty acid ester, which was then stirred to obtain a uniformly dissolved solution. This solution was filled into hard capsule of Japanese Pharmacopoeia capsule in an amount of 100 mg per capsule to obtain Tamibarotene capsule preparation containing 1 mg of Tamibarotene. They were subsequently sealed and then made into finished products by PTP packaging.

Example 16

Tamibarotene drug substance in an amount of 10 g was added to 990 g of glycerol fatty acid ester (DGO-80, manufactured by Nikko Chemicals Co., Ltd.) which was then stirred to obtain a uniformly dissolved solution. This solution was filled into oval soft capsules in an amount of 100 mg per capsule to obtain Tamibarotene capsule preparation containing 1 mg of Tamibarotene. They were subsequently made into finished products by PTP packaging.

Example 17

Tamibarotene drug substance in an amount of 10 g was added to 990 g of sorbitan fatty acid ester (POEM O-80V, manufactured by Riken Vitamin Co., Ltd.), which was then stirred to obtain a uniformly dissolved solution. This solution was filled into oval soft capsules in an amount of 100 mg per capsule to obtain Tamibarotene capsule preparation containing 1 mg of Tamibarotene. They were subsequently made into finished products by PTP packaging.

Example 18

Tamibarotene drug substance in an amount of 10 g was added to 990 g of olive oil, which was then stirred to obtain a uniformly dissolved solution. This solution was filled into oval soft capsules in an amount of 100 mg per capsule to obtain Tamibarotene capsule preparation containing 1 mg of Tamibarotene. They were subsequently made into finished products by PTP packaging.

Example 19

Tamibarotene drug substance in an amount of 10 g was added to 990 g of sunflower seed oil, which was then stirred to obtain a uniformly dissolved solution. This solution was filled into oval soft capsules in an amount of 100 mg per capsule to obtain Tamibarotene capsule preparation containing 1 mg of Tamibarotene. They were subsequently made into finished products by PTP packaging.

Example 20

Tamibarotene drug substance in an amount of 10 g was added to 990 g of soybean oil, which was then stirred to obtain a uniformly dissolved solution. This solution was filled into oval soft capsules in an amount of 100 mg per capsule to obtain Tamibarotene capsule preparation containing 1 mg of Tamibarotene. They were subsequently made into finished products by PTP packaging.

Example 21

Tamibarotene drug substance in an amount of 10 g was added to 990 g of corn oil, which was then stirred to obtain a uniformly dissolved solution. This solution was filled into oval soft capsules in an amount of 100 mg per capsule to obtain Tamibarotene capsule preparation containing 1 mg of Tamibarotene. They were subsequently made into finished products by PTP packaging.

Example 22

Tamibarotene drug substance in an amount of 10 g was added to 891 g of propylene glycol fatty acid ester, which was then stirred to dissolve uniformly, and further 99 g of olive oil was added thereto and stirred to obtain a uniformly dissolved solution. This solution was filled into oval soft capsules in an amount of 10 mg per capsule to obtain Tamibarotene capsule preparation containing 1 mg of Tamibarotene. They were subsequently made into finished products by PTP packaging.

Example 23

Tamibarotene drug substance in an amount of 10 g was added to 891 g of propylene glycol fatty acid ester, which was then stirred to dissolve uniformly, and further 99 g of soybean oil was added thereto and stirred to obtain a uniformly dissolved solution. This solution was filled into oval soft capsules in an amount of 100 mg per capsule to obtain Tamibarotene capsule preparation containing 1 mg of Tamibarotene. They were subsequently made into finished products by PTP packaging.

Example 24

Tamibarotene drug substance in an amount of 10 g was added to 891 g of propylene glycol fatty acid ester, which was then stirred to dissolve uniformly, and further 99 g of corn oil was added thereto and stirred to obtain a uniformly dissolved solution. This solution was filled into oval soft capsules in an amount of 100 mg per capsule to obtain Tamibarotene capsule preparation containing 1 mg of Tamibarotene. They were subsequently made into finished products by PTP packaging.

Example 25

Tamibarotene drug substance in an amount of 10 g was added to 891 g of propylene glycol fatty acid ester, which was then stirred to dissolve uniformly, and further 99 g of sunflower seed oil was added thereto and stirred to obtain a uniformly dissolved solution. This solution was filled into oval soft capsules in an amount of 100 mg per capsule to obtain Tamibarotene capsule preparation containing 1 mg of Tamibarotene. They were subsequently made into finished products by PTP packaging.

Example 26

Tamibarotene drug substance in an amount of 10 g was added to 495 g of propylene glycol fatty acid ester, which was then stirred to dissolve uniformly, and further 495 g of olive oil was added thereto and stirred to obtain a uniformly dissolved solution. This solution was filled into oval soft capsules in an amount of 100 mg per capsule to obtain Tamibarotene capsule preparation containing 1 mg of Tamibarotene. They were subsequently made into finished products by PTP packaging.

Example 27

Tamibarotene drug substance in an amount of 10 g was added to 99 g of propylene glycol fatty acid ester, which was then stirred to dissolve uniformly, and further 891 g of olive oil was added thereto and stirred to obtain a uniformly dissolved solution. This solution was filled into oval soft capsules in an amount of 100 mg per capsule to obtain Tamibarotene capsule preparation containing 1 mg of Tamibarotene. They were subsequently made into finished products by PTP packaging.

Example 28

Tamibarotene drug substance in an amount of 20 g was added to 881 g of propylene glycol fatty acid ester, which was then stirred to dissolve uniformly, and further 99 g of olive oil was added thereto and stirred to obtain a uniformly dissolved solution. This solution was filled into oval soft capsules in an amount of 100 mg per capsule to obtain Tamibarotene capsule preparation containing 2 mg of Tamibarotene. They were subsequently made into finished products by PTP packaging.

The invention claimed is:

1. A Tamibarotene capsule preparation, which encapsulates a composition comprising propylene glycol fatty acid esters as a base and Tamibarotene as an active ingredient dissolved in said base.

2. The Tamibarotene capsule preparation according to claim 1, comprising 0.1-50 mg/mL of said Tamibarotene relative to said propylene glycol fatty acid esters.

3. The Tamibarotene capsule preparation according to claim 1, which is formulated for oral administration.

4. The Tamibarotene capsule preparation according to claim 1, wherein the capsule is a soft capsule or hard capsule.

5. The Tamibarotene capsule preparation according to claim 1, which is formulated for use in treating a blood cancer or a solid cancer.

6. The Tamibarotene capsule preparation according to claim 2, wherein the capsule is a soft capsule or hard capsule.

7. The Tamibarotene capsule preparation according to claim 2, which is formulated for use in treating a blood cancer or a solid cancer.

8. The Tamibarotene capsule preparation according to claim 2, wherein said propylene glycol fatty acid esters are selected from the group consisting of propylene glycol monooleate and propylene glycol di(capryl, caprylic acid) ester.

9. The Tamibarotene capsule preparation according to claim 2, wherein said propylene glycol fatty acid ester is propylene glycol di(capryl, caprylic acid)ester.

* * * * *